United States Patent [19]

Atala et al.

[11] Patent Number: 5,304,123
[45] Date of Patent: Apr. 19, 1994

[54] DETACHABLE BALLOON CATHETER FOR ENDOSCOPIC TREATMENT OF VESICOURETERAL REFLUX

[75] Inventors: Anthony Atala, Newton; James Mandell, Brookline, both of Mass.

[73] Assignee: Children's Medical Center Corporation, Boston, Mass.

[21] Appl. No.: 782,058

[22] Filed: Oct. 24, 1991

[51] Int. Cl.$^5$ .......................................... A61M 29/02
[52] U.S. Cl. ................................. 604/54; 606/192; 604/96
[58] Field of Search ............... 606/191, 192, 195, 108; 604/96, 54; 623/1, 12; 128/898

[56] References Cited

U.S. PATENT DOCUMENTS

| | | |
|---|---|---|
| 3,831,585 | 8/1974 | Brondy et al. |
| 4,282,875 | 8/1981 | Serbinenko et al. |
| 4,311,146 | 1/1982 | Wonder .................. 128/325 |
| 4,327,734 | 5/1982 | White, Jr. .................. 128/325 |
| 4,334,327 | 6/1982 | Lymem et al. .................. 623/12 |
| 4,341,218 | 7/1982 | Ü128 .................. 325/ |
| 4,346,712 | 8/1982 | Handa et al. .................. 128/325 |
| 4,364,392 | 12/1982 | Strother et al. .................. 128/325 |
| 4,402,319 | 9/1983 | Handa et al. .................. 604/103 |
| 4,441,495 | 4/1984 | Hicswa .................. 128/325 |
| 4,517,979 | 5/1985 | Pecenica .................. 128/325 |
| 4,520,823 | 6/1985 | LeVeen et al. .................. 128/348.1 |
| 4,545,367 | 10/1985 | Tecci .................. 128/1 R |
| 4,773,393 | 9/1988 | Haber et al. .................. 606/195 |
| 4,802,479 | 2/1989 | Haber et al. .................. 606/192 |
| 4,832,680 | 5/1989 | Haber et al. .................. 606/192 |
| 5,007,898 | 4/1991 | Rosenbluth et al. .................. 606/192 |
| 5,071,429 | 12/1991 | Pinchuk et al. .................. 604/54 |

FOREIGN PATENT DOCUMENTS 2185400  7/1987  United Kingdom.

OTHER PUBLICATIONS

Atala et al., "Management of Primary Vesicoureteral Reflux", Infections in Urology, Mar./Apr. 1990, pp. 39-43.

Primary Examiner—Edgar S. Burr
Assistant Examiner—Ren Yan
Attorney, Agent, or Firm—Thomas J. Engellenner; Elizabeth A. Hanley

[57] ABSTRACT

Methods and systems for treatment of vesicoureteral reflux are disclosed in which a detachable balloon catheter is incorporated into a endoscopic instrument, such as a cystoscopic needle. The needle is directed through the cystoscope and inserted into the subureteral region of the refluxing ureter. A catheter or similar delivery device is inserted into the subureteral region, carrying a balloon. The balloon is then inflated, preferably filled with an inert biocompatible material, and then sealed. After inflation, the balloon is detached and left in the pocket such that the junction of the bladder and ureter is reconfigured to prevent reflux.

19 Claims, 3 Drawing Sheets

DETACHABLE BALLOON CATHETER FOR ENDOSCOPIC TREATMENT OF VESICOURETERAL REFLUX

BACKGROUND OF THE INVENTION

The technical field of this invention is treatment of urological defects and, in particular, the treatment of vesicoureteral reflux.

The discharge of urine via the urinary tract is essential to the maintenance of healthy kidney functions. In the normal individual, urine flows from the kidneys through the ureters into the bladder. From there it is periodically released via the urethra. The terminus of the ureter at the bladder normally provides a competent sphincter which insures that urine flows from the ureter to the bladder. However, if this junction is impaired, vesicoureteral reflux can occur wherein urine from the bladder can return to the kidney, particularly during voiding or when pressure is exerted upon the bladder.

Vesicoureteral reflux can cause renal damage or even renal failure either directly as a result of high pressures transmitted to the kidney or indirectly as a result of infections introduced by retromigration of bacteria into the kidneys. These problems can be particularly acute in newborns and infants when incompetent ureterovesical junctions are present. In some children, the risk of kidney damage can be reduced by antibiotic therapies and minor reflux problems will disappear over time with increased developmental maturity.

However, when vesicoureteral reflux is severe, surgery has often been necessary to repair the disfunctional junction. In most of these approaches, the ureter is dissected from the bladder and re-implanted to lengthen or otherwise restrict the submucosal tunnel. By reconfiguring the tunnel, closure of the ureteral lumen can be markedly improved as a result of intravesical pressure as the bladder fills.

Unfortunately, these open surgical procedures always carry risks, including collateral damage to other urological structures and the possible introduction of further infectious agents. These risks are particularly pronounced when surgery is required on newborns or infants.

The endoscopic treatment of reflux was first introduced in 1981 by Matouschek when he injected polytetrafluoroethylene (Teflon) paste in the suburetal region of a patient. In this approach, a bolus of Teflon paste is introduced into the suburetal region to restrict or reshape the submucosal tunnel. In a manner similar to surgical procedures, the effective length of the submucosal tunnel is increased and effective closure, as the bladder fills, is likewise achieved. This technique was popularized by O'Donnell and Puri, and has now been utilized to treat vesicoureteral reflux in over 8000 children.

The use of Teflon paste in the pediatric population is not without controversy due to evidence of Teflon particle migration to the lungs and nodes and granuloma formation in both animal models and in humans. Nonetheless, there are definite advantages in treating these patients endoscopically. The method is simple and can be completed in less than 15 minutes, it has a success rate of over 85% with a low morbidity, and can be performed in an outpatient basis.

Various other substances have been proposed as safer alternate implant materials, including collagen, autologous fat and fibroblast injections, polyvinyl alcohol foam (Ivalon) and glass; however each has its disadvantages. Volume loss has been identified as a problem with collagen, autologous fat and fibroblast injections. Granuloma formation with possible latent carcinogenic effects has been associated with Ivalon and glass particles as well as Teflon paste.

There exists a need for better methods and systems for treatment of vesicoureteral reflux and related urological disorders. In particular, approaches that avoid open reconstructive surgery while providing effective control of urinary reflux would satisfy a long-felt need in the field, especially in the treatment of neonatal birth defects.

SUMMARY OF THE INVENTION

Methods and systems for treatment of vesicoureteral reflux are disclosed in which a detachable balloon catheter is incorporated into a endoscopic instrument, such as a cystoscopic needle. The needle is directed through the cystoscope and inserted into the subureteral region of the refluxing bladder to establish a pocket. A catheter or similar delivery device can be inserted into this pocket in the subureteral region, carrying a balloon. The balloon is then inflated, preferably filled with an inert biocompatible material, and then sealed. After inflation, the balloon is detached and left in the pocket such that the junction of the bladder and ureter is reconfigured to prevent reflux.

The methods and systems of the present invention provide implant materials which can be delivered endoscopically, and which conserve their volume, and are substantially non-migratory and non-antigenic.

In one aspect of the invention, methods are disclosed in which a pocket is established in the subureteral region, preferably between the mucosal and submucosal tissue layers. A balloon structure is then introduced into the pocket and inflated (e.g., by filling the structure with a biocompatible material, such as a polymerizable solution). The contents of the balloon preferably are solidified, and then the balloon is sealed, and left in place. By positioning the balloon within the pocket, the ureter is reconfigured to provide a competent ureterovesical junction.

In another aspect of the invention, systems are disclosed for performing non-surgical procedures for the treatment of vesicoureteral reflux, employing a cystoscope, a positioning means for establishing a pocket in the subureteral region, and a means for deploying a detachable balloon structure within the pocket to reposition the ureteral terminus, thereby alleviating reflux.

Various cystoscopes can be used in the present invention and are commercially available from various sources including, for example, Karl Storz Co. (Culver, Calif.); and Olympus Corporation of (Wilmington, Mass.).

The positioning means useful in establishing a subureteral pocket can be a cystoscopic needle, e.g., a 19 gauge needle which is small enough to fit within standard cystoscopic equipment. In one system, a thin walled cystoscopic needle was obtained from Cook Urological Co. (Spencer, Ind.) which had a 19 gauge outer diameter but had the inner diameter of a standard 18 gauge needle (0.036 inches).

Balloon structures useful in the present invention can be formed from silicone or similar substantially non-antigenic elastic materials. The uninflated balloons preferably are sized to fit unto the tip of a catheter which can pass readily through the lumen of the positioning device (e.g., a cystoscopic needle).

The balloon structures can take various forms but preferably include a sealing mechanism which seals the balloon upon inflation. The sealing mechanism can be achieved, for example, by a constrictive collar, or a lip seal, or both.

The balloon can be delivered by a catheter which is inserted through the needle or positioning means to the site where the balloon is to be inflated. In one preferred embodiment, the catheter provides a means for not only inflating the balloon but also means for filling the balloon with a biocompatible material. Catheters suitable for use in the present invention are available from various sources including, for example, Interventional Therapeutics (San Francisco, Calif.).

Various materials can be used to fill the balloon, including collagen, autologous fat or cellular extracts, or an inert polymer. In one embodiment, the balloon is filled with a polymerizable solution, such as an acrylic solution which solidifies in situ. In a preferred embodiment, the polymerizable solution is a solution of hydroxyethyl methylacrylate (HEMA) which is cured to a solid form by the addition of ferrous sulfate and hydrogen peroxide.

The invention will next be described in connection with certain illustrated embodiments; however, it should be clear that those skilled in the art can make various modifications, additions and subtractions without departing from the spirit or scope of the invention. For example, although the invention is specifically described in connection with the treatment or vesicoureteral reflux, it should be clear that the invention is applicable to other treatment protocols.

DETAILED DESCRIPTION

Figure 1:
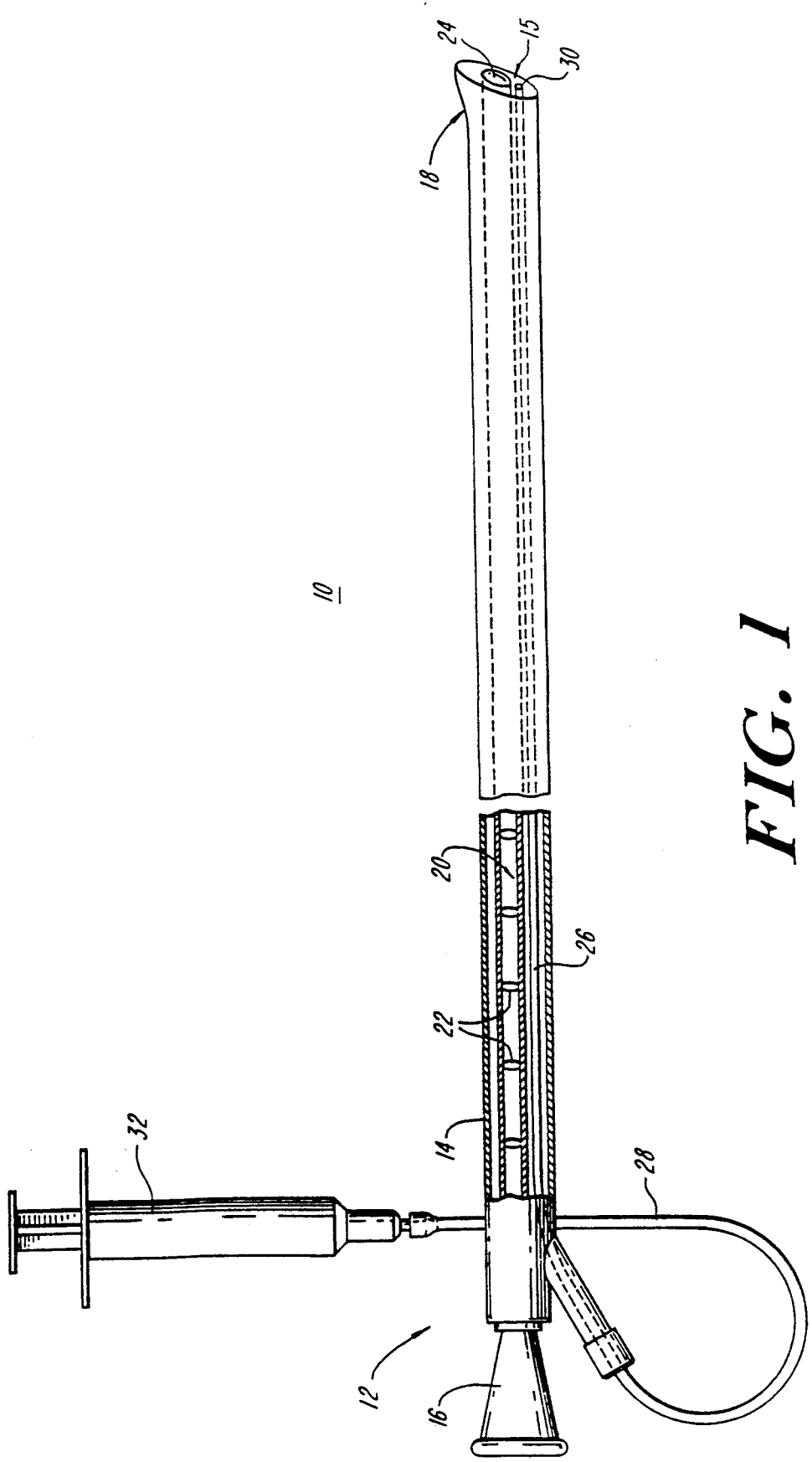
FIG. 1 is schematic diagram of a system according to the invention.

FIG. 1 shows a system 10 for treatment of vesicoureteral reflux including a cystoscope 12 having a outer sheath 14 and an inner lumen 15. The cystoscope includes an eyepiece or other viewing port (e.g., a video adaptor) 16 in optical communication with the distal tip 18 of the cystoscope. In the illustrated embodiment, an optical relay mechanism 20, including for example, a series of lenslets 22 and a distal cystoscopic lens 24 are disposed within the lumen 15 of the cystoscope 12.

The cystoscope 12 further includes a positioning means, e.g., a cystoscopic needle 26 for positioning a balloon structure 30 in the subureteral region of a refluxing bladder. The balloon structure is preferably connected to a catheter 28 which passes through the positioning means 26 and serves to inflate the balloon structure. In the illustrated embodiment, the catheter is connected to a polymerizable solution supply, e.g., a syringe 32.

Figure 2A:
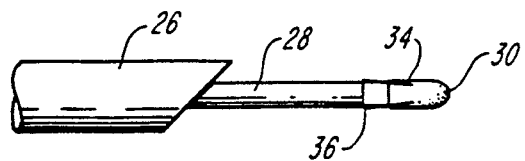
FIG. 2A is a more detailed schematic diagram of the distal tip of the system of FIG. 1 prior to inflation of the balloon structure.
Figure 2B:
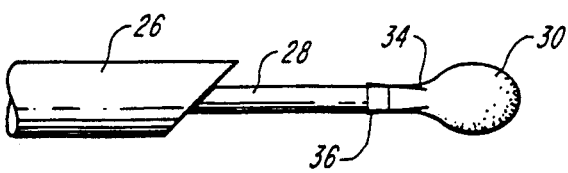
FIG. 2B is another diagram of the system of FIG. 2A in which the balloon means is being inflated.
Figure 2C:
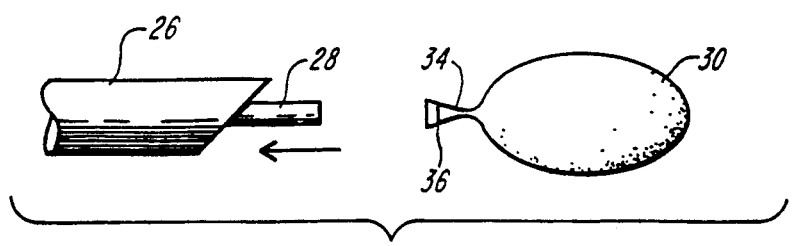
FIG. 2C is another diagram of the system of FIG. 2B in which an inflated balloon means has been detached.

In FIGS. 2A-2C, the operation of the positioning means 26 and the balloon structure 30 is illustrated in more detail. As shown in FIG. 2A, the end of cystoscopic needle 26 is positioned at a site where inflation and implantation of the balloon structure is desired. Catheter 28 with balloon 30 at its tip is then advanced through the needle 26 into place at the site, e.g. in the subureteral region, and then inflated as shown in FIG. 2B.

The balloon structure 30 preferably includes at least one sealing mechanism, such a lip or flap seal 34 or a constrictive collar 36, which provide for self-sealing of the balloon means upon inflation. Such sealing mechanisms operate to expel and/or close the balloon when a certain inflation state is reached. FIG. 2C shows a fully inflated balloon which has been detached from the catheter 28, such that the catheter 28 and needle 26 can be withdrawn from the implant site.

Figure 3A:
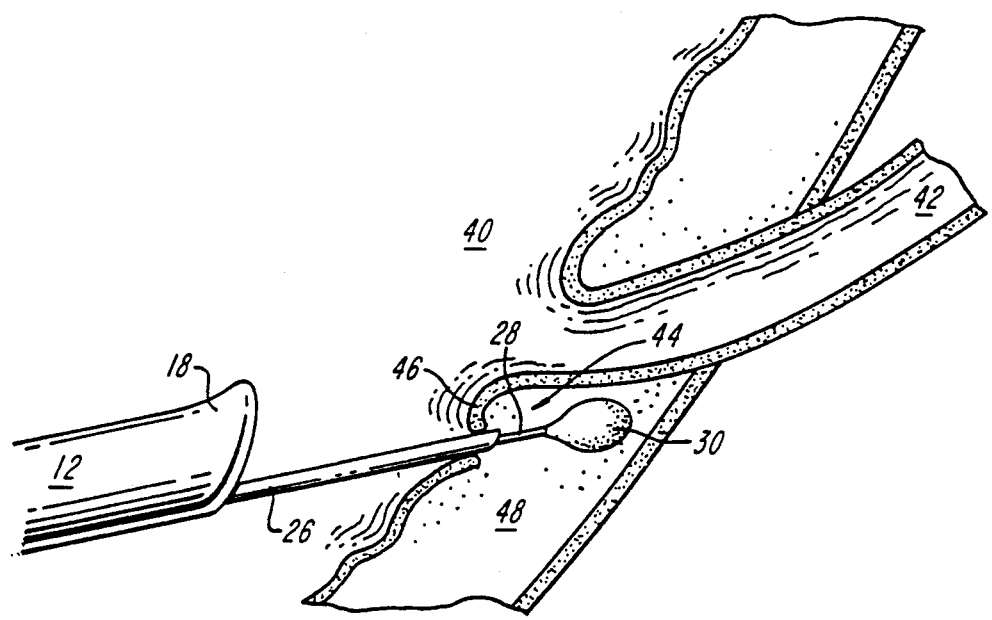
FIG. 3A is a schematic diagram illustrating an initial stage of a method according to the invention in which a pocket is established within the subureteral region.

In use, the invention can be practiced by introducing the cystoscope 12 into the bladder 40 and, as shown in FIG. 3A, inserting the needle 26 into the subureteral region of the refluxing ureter 44 (e.g. between the mucosal and submucosal tissue layers 46, 48, respectively). The balloon 30 with the attached delivery catheter 28 then is inserted through the core of the needle 26 and placed in the subureteral region. After inflation of the balloon, e.g., with a polymerizable solution, the needle is withdrawn from the subureteral tissue leaving the balloon in place.

Figure 3B:
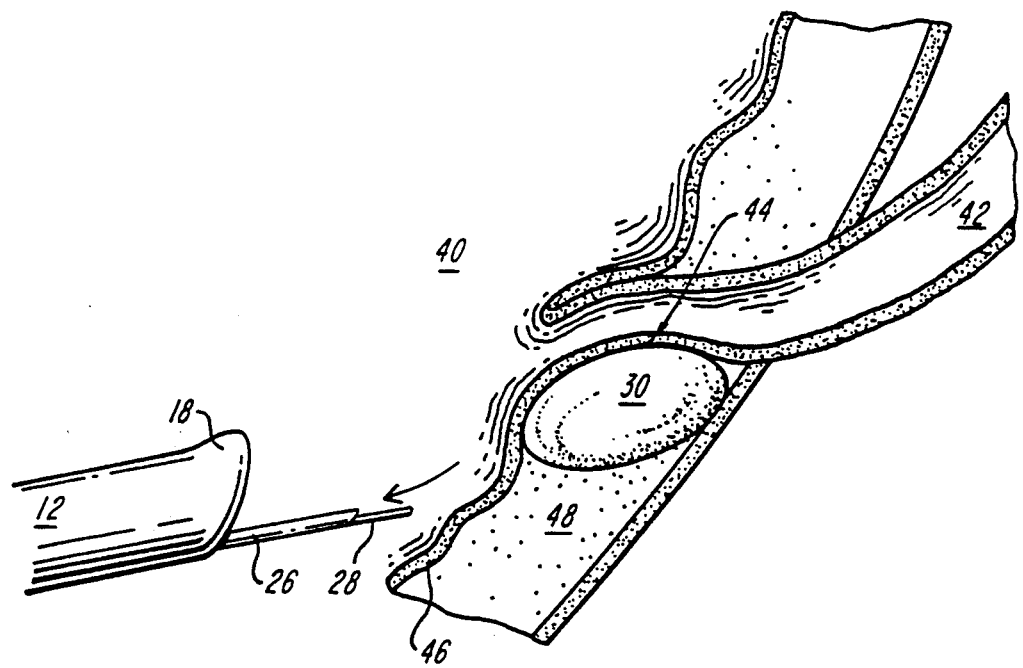
FIG. 3B is a further schematic diagram illustrating a subsequent stage in the method of FIG. 3A in which a balloon is inflated within the pocket and then detached.

Hydroxyethyl methylacrylate (HEMA), a hydrophylic polymer compatible with silicone and which solidifies within 60 minutes after the addition of ferrous sulfate and hydrogen peroxide, is particularly useful as a filling material for the balloon 30. HEMA can be injected through the catheter 28 to inflate the balloon 30, while endoscopically visualizing the balloon compressive effect on its surrounding tissue. The catheter is then pulled, leaving the self-sealing detachable balloon in place, as shown in FIG. 3B. The compressive effect of the inflated balloon 30 is to reconfigure the ureteral tunnel 44 so as to minimize the likelihood of reflux.

The invention will next be described in connection with certain non-limiting experimental protocols.

EXAMPLES

A system similar to that shown in FIG. 1 was constructed with catheter having a length of about 100 centimeters and the diameter of about 2.0 French. The balloon design included a small lip seal valve closure mechanism and had an uninflated diameter of about 0.034 inches. A thin walled cystoscopic needle was obtained from Cook Urological (Spencer, Ind.) which had a 19 gauge outer diameter but had the inner diameter of a standard 18 gauge needle (0.036 inches). HEMA was used as the filling material for the balloons. Infused through the deliver catheter and into the balloon HEMA progresses from a water like liquid state, to a semi-solid gel form and ultimately solidifies within the balloon shell. Polymerization time is controlled by varying the ingredients necessary for the reaction to occur. An estimated time to cure of 60 minutes was achieved by utilizing a solution composed of 64.5% of HEMA, 32.2% of hydrogen peroxide and 3.25% of ferrous ammonium sulfate.

Pigs were chosen for this study because of the similarities between porcine and human kidneys. The Hanford minipig was used for the convenience of its smaller size. Preoperative intravenous pyelograms (IVP's) and cystograms with Conray (Mallinkrodt, Inc., St. Louis, Mo.) were performed in 5 of the 6 minipigs.

Reflux was created in 6 female Hanford minipigs by unroofing the ureters bilaterally. This was done with the standard technique of open surgery in two minipigs. However in the other 4 we attempted and were successful in creating reflux endoscopically utilizing laparoscopic scissors through a 14 French cystoscope.

Four to 6 weeks later the presence of bilateral reflux was confirmed with a cystogram and the balloon was implanted unilaterally in the subureteral region. This was done with open surgery in the first minipig and endoscopically through a 19 gauge needle and a 15 Fr. cystoscope in 5 minipigs. A repeat cystogram and IVP were performed 2 to 4 weeks after implantation.

Serial cystograms, ultrasounds, and IVP's were performed at 4 to 6 week intervals until sacrifice. The six minipigs were sacrificed at 4(1), 8(2), 12(2), and 24(1) weeks after balloon implantation. The bladder balloon implant sites were resected and analyzed macroscopically and microscopically. Histologic analyses of the bladder, ureters, regional lymph notes, kidneys, spleen, liver and the tissue surrounding the balloon implant sites were performed.

All minipigs which had preoperative studies had no evidence of reflux as demonstrated by a cystogram and no evidence of obstruction as demonstrated by ultrasonography or IVP'S. Four to six weeks after unroofing the ureters bilaterally, cystograms confirmed the presence of bilateral reflux, and IVP's and renal ultrasonography demonstrated no evidence of obstruction in each animal.

Cystography was again performed 2 to 4 weeks after balloon implantation in all animals. This demonstrated resolution of reflux in the treated ureter and persistence of reflux in the opposite untreated ureter. The serial cystograms, ultrasounds, and IVP's performed at 4 to 6 week intervals showed persistence of reflux in the untreated side and continued effectiveness of the balloon in the implanted ureter without reflux or evidence of obstruction.

After sacrifice, gross inspection of the bladder implant site showed no evidence of extrusion or abscess formation in any of the minipigs. Microscopic analyses of the tissues surrounding the balloon implant showed mild inflammation. A fibrotic reaction was also evident between the balloon shell and the ureteral tissue. Tissue sections from the lymph nodes, kidneys, liver and spleen showed no evidence of particle migration or inflammatory reaction.

What we claim is:

1. A method of treating vesicoureteral reflux comprising;
   providing a cystoscopic system comprising a sheath, a viewing means for viewing a distal site and a positioning element extending longitudinally through the sheath:
   inserting the sheath through the urethra of a patient;
   passing an uninflated, detachable balloon attached to a catheter through a lumen of the positioning element to a subureteral region of a reflux-prone bladder; and
   inflating and detaching the balloon from the catheter in place such that the ureter is repositioned to provide a competent ureterovesical junction while endoscopically visualizing the compressive effect of the balloon on the surrounding tissue.

2. The method of claim 1 wherein the method further comprises establishing a pocket for insertion of the balloon within the subureteral region.

3. The method of claim 1 wherein the balloon is inserted between the mucosal and submucosal layers of the bladder.

4. The method of claim 1 wherein the method further comprises filling the balloon with a biocompatible material.

5. The method of claim 4 wherein the filling material is a polymerizable solution.

6. A method as claimed in claim 5 wherein the polymerizable solution is hydroxyethyl methacrylate.

7. The method of claim 4 wherein the method further comprises allowing the filling material to solidify.

8. The method of claim 1 wherein the method further comprises inflating the balloon to reconfigure the ureteral tunnel.

9. The method of claim 1 wherein the positioning element is a hypodermic needle.

10. The method of claim 1 wherein the lumen of the positioning element has an inside diameter of less than about 0.036 inches.

11. A system for the deployment of a detachable balloon comprising:
    a cystoscopic system comprising a sheath, a viewing means for viewing a distal site and a positioning element extending longitudinally through the sheath; and
    a balloon catheter including an uninflated, detachable balloon attached thereto, said positioning element having a longitudinal lumen therethrough, means for passing said balloon through said lumen of said positioning element, and means for inflating and detaching said balloon from said balloon catheter.

12. The system of claim 11 wherein the system comprises a means for establishing a pocket in the subureteral region.

13. The system of claim 11 further comprises a means for filling the balloon with a biocompatible material.

14. The system of claim 11 wherein the balloon comprises an elastic inflatable element and a sealing means for sealing the balloon following inflation.

15. The system of claim 14 wherein the elastic inflatable element comprises a silicone rubber balloon.

16. The system of claim 14 wherein the sealing means comprises a constrictive collar.

17. The system of claim 14 wherein the sealing means comprises a lip seal.

18. The system of claim 11 wherein the positioning element is a hypodermic needle.

19. The system of claim 11 wherein the lumen of the positioning element has an inside diameter of less than about 0.036 inches.

* * * * *